United States Patent [19]

Matzoll, Jr. et al.

[11] Patent Number: 4,853,879
[45] Date of Patent: Aug. 1, 1989

[54] AUTOMATED PAINT FILM CHARACTERIZATION SYSTEM

[76] Inventors: Robert J. Matzoll, Jr., 711 Kentucky St., Rochester Hills; Deborah C. Pawlaczyk, 345 Terry St., Rochester, both of Mich. 48063

[21] Appl. No.: 33,656
[22] Filed: Apr. 3, 1987
[51] Int. Cl.⁴ .................... G06F 15/46; G01N 21/00
[52] U.S. Cl. .................... 364/552; 356/448; 356/73; 364/526
[58] Field of Search .............. 358/106, 107; 364/550–552, 526; 356/446, 445, 237, 402, 448, 73; 250/571

[56] References Cited

U.S. PATENT DOCUMENTS

| | | | |
|---|---|---|---|
| 3,704,362 | 11/1972 | Kolby et al. | 364/552 |
| 4,476,489 | 10/1984 | Weltlich et al. | 358/107 |
| 4,505,589 | 3/1985 | Ott et al. | 356/402 |
| 4,527,898 | 7/1985 | Stapleton | 356/446 |
| 4,539,647 | 9/1985 | Kaneko et al. | 364/526 |
| 4,583,858 | 4/1986 | Lebling et al. | 356/402 |
| 4,707,138 | 11/1987 | Coatney | 356/402 |
| 4,711,580 | 12/1987 | Venable | 356/406 |

FOREIGN PATENT DOCUMENTS 0960544  9/1982  U.S.S.R. .................... 356/445

Primary Examiner—Parshotam S. Lall
Assistant Examiner—J. A. Melnick
Attorney, Agent, or Firm—Krass & Young

[57] ABSTRACT

A system for characterizing and monitoring a coated surface includes a sensor head which measures a plurality of characteristics of the surface and a signal processor which compares the measured characteristics with stored data so as to assess the quality of the coated surface. The system provides an alarm or other indication if the surface is not up to acceptable standards. The system has great utility in the inspection of painted surfaces particularly in a high volume mass production process such as the fabrication of automobiles.

17 Claims, 3 Drawing Sheets

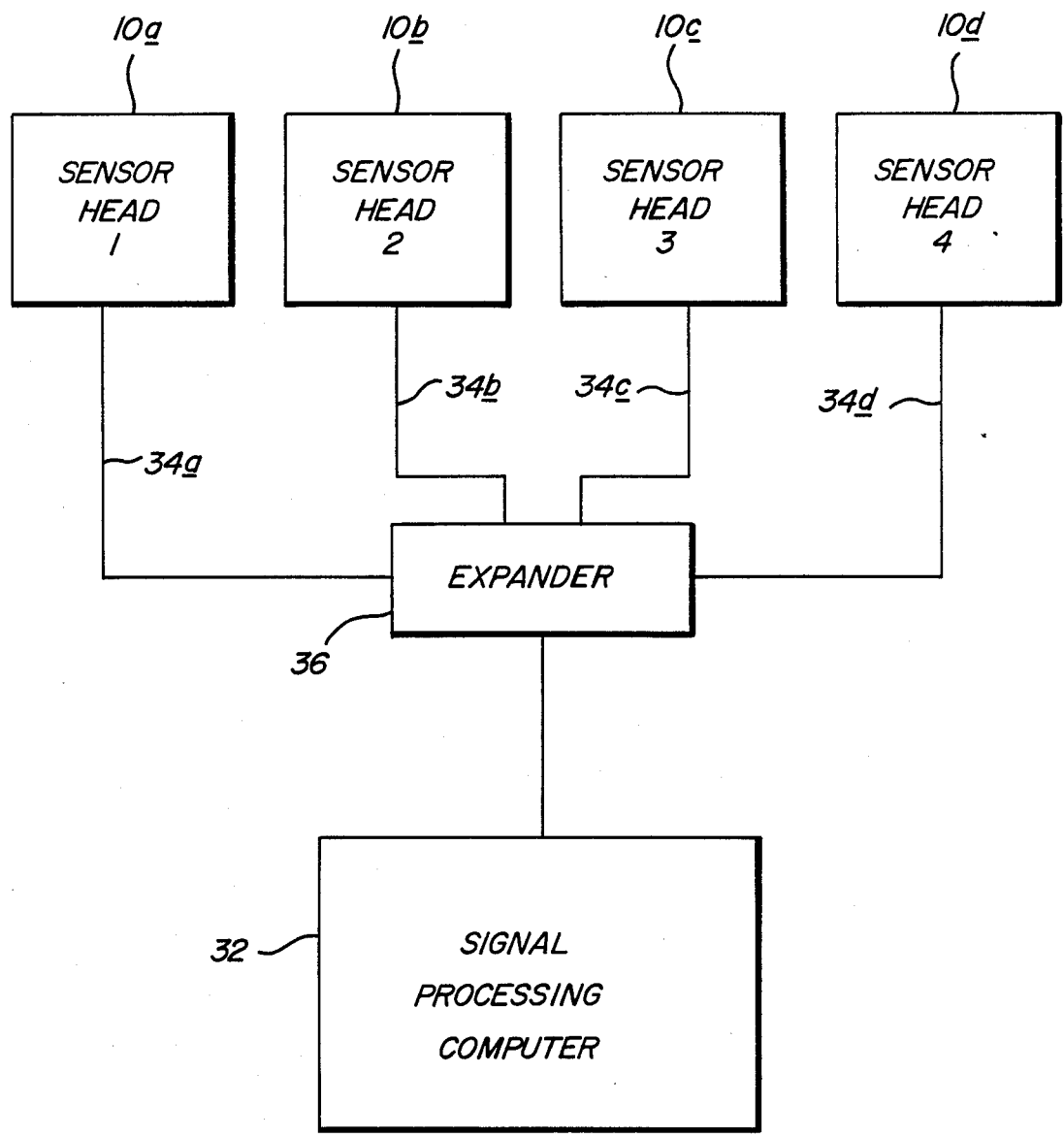

AUTOMATED PAINT FILM CHARACTERIZATION SYSTEM

FIELD OF THE INVENTION

The present invention relates to measuring systems in general; and in particular to measuring systems adapted to measure a plurality of parameters of a coated surface such as a painted or plated surface so as to characterize or monitor the physical appearance thereof. The present invention has significant utility in a production process insofar as it allows for the continuous, real time monitoring of various visual characteristics of items being produced.

BACKGROUND OF THE INVENTION

In a production process it is frequently necessary to monitor and control visual characteristics of the surfaces of objects. Such control is necessary to assure that the proper shade of paint or other coating has been applied and that such application is uniform and proper thickness. Monitoring is also necessary to assure that the appropriate surface finish, as for example a gloss or matte finish is present. The necessity of maintaining such control is particularly significant in both the manufacture of objects which are assembled from a variety of separate parts and in the fabrication of objects having large surface areas. In the instances where a number of parts are assembled it is generally desired that visual uniformity of the parts be maintained, and in instances where large objects are being manufactured it is generally necessary to maintain control so as to assure uniformity of color, texture and finish thereacross. The manufacture of automobiles involves both manufacturing modalities and the need for the system disclosed hereinbelow is particularly great in that industry.

The most immediately apparent feature of an automobile is its exterior finish and even minor mismatches or flaws in the paint and finish thereof detract significantly from its appearance. Accordingly, automobile manufacturers carefully monitor the visual characteristics of the paint and finish of automobiles during their manufacture. Such inspection generally is carried on by trained personnel and frequently involves the use of a number of separate, specialized measuring tools. For example, colorimeters may be employed to measure the color value of a painted surface to assure that the paint has the proper hue, saturation and lightness; as well as to assure that differing portions of the automobile have the same color values. Similarly, other measurement tools such as gloss meters or distinctness of image meters may be employed to assure that the proper reflectivity is present in the painted surface.

Heretofore such measurements were expensive, time consuming and difficult to implement in a mass production system. It will be seen then what is needed is an inspection system for monitoring visual characteristics of surfaces, particularly coated surfaces such as painted or plated surfaces, which system is compatible with a mass production process, does not require skilled personnel for operation or interpretation of data produced thereby. Furthermore, such a system should be capable of measuring a variety of surface parameters and be adapted to determine if the coated surface meets a desired group of specifications.

The present invention provides such an inspection system and has utility in mass production processes where it is necessary or desirable to inspect plated, polished, painted or other coated surfaces to assess a plurality of parameters thereof. The system disclosed herein has significant utility in mass production processes for the manufacture of automobiles, aircraft, architectural panels, and the like.

SUMMARY OF THE INVENTION

There is disclosed herein a system for characterizing and monitoring a coated surface. The system includes a sensor head adapted to measure a plurality of characteristics of the surface and provide a signal corresponding to the value of each of the characteristics. The system further includes a signal processor adapted to receive the signal from the sensor head and analyze it to determine the values of the characteristics of the coated surface, compare the determined values with stored data so as to assess the acceptability of the coated surface, store the results of the comparison and provide an indication if the coated surface is not acceptable.

The sensor head may include a plurality of separate sensor units, each adapted to measure one characteristic of the coated surface. In one embodiment, the sensor head is adapted to characterize and monitor a painted surface and includes four sensor units therein adapted to measure gloss, distinctness of image, film build and color respectively. In some instances a sensor head may include a microprocessor and may be further adapted to store the signal provided thereby for later transmission to the signal processing means. In some instances, the sensor head may include a display device adapted to display at least one of the measured characteristics, as well as a position indicator adapted to indicate proper placement of the head or the coated surface.

The signal processing means may further include a computer. In yet other instances, the system may include a plurality of sensor heads all communicating with an expander adapted to receive signals from the heads, store the signals and sequentially transmit them to the computer of the signal processor. The signal processor may also include data storage means therein for storing a data base utilized in the evaluation of the coating. The data base may be selected by user input, or in response to one or more of the parameters measured by the sensor head.

In one embodiment having particular utility in the mass production of automobiles, the sensor head is mounted in conjunction with a counterbalance support so that it may be readily positioned proximate a coated surface.

BRIEF DESCRIPTION OF THE DRAWINGS

FIG. 3 is a stylized block diagram illustrating an embodiment of the invention where a plurality of sensor heads are utilized.

DETAILED DESCRIPTION OF THE DRAWINGS

Figure 1:
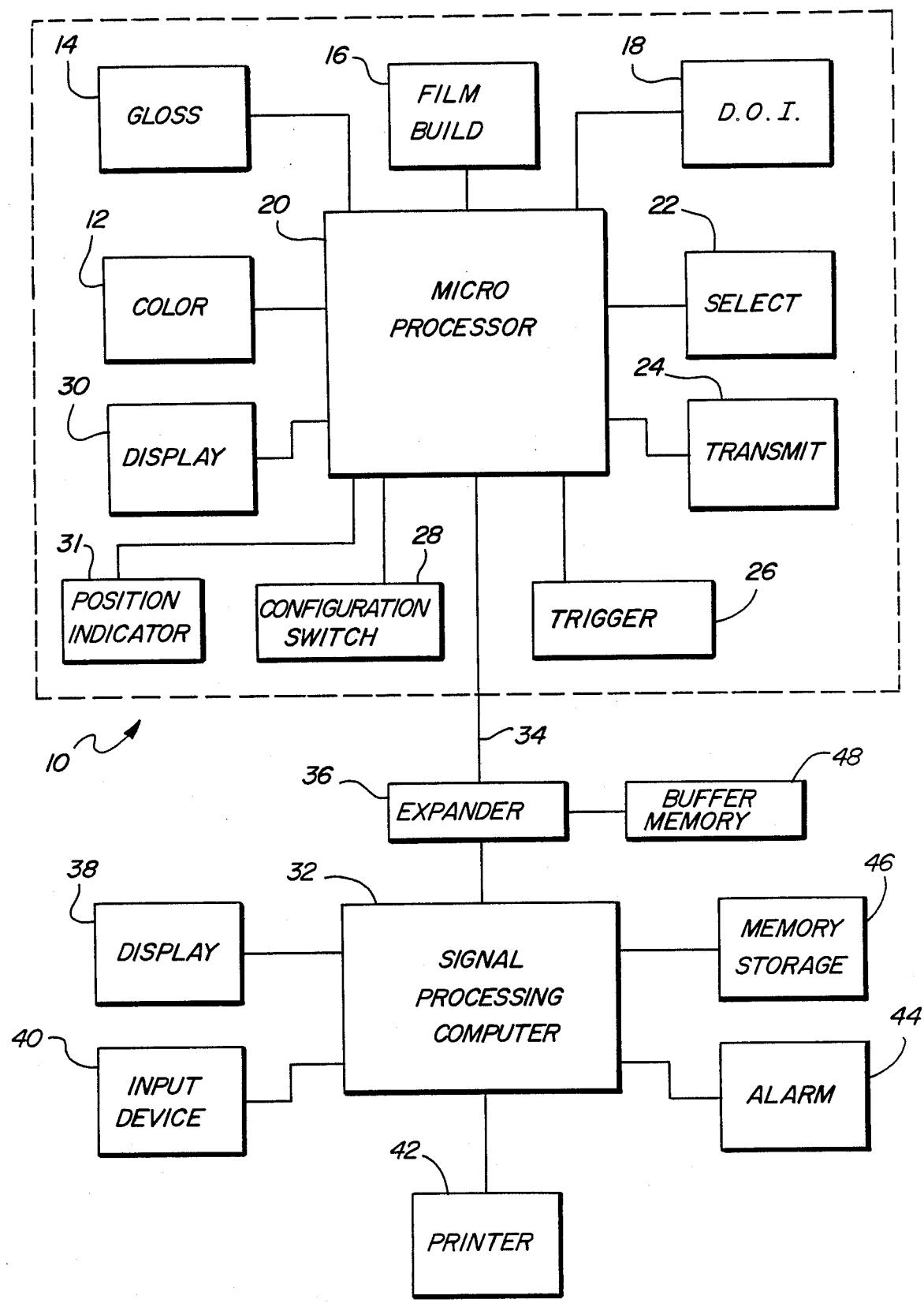
FIG. 1 is a stylized block diagram illustrating the components of one embodiment of coated surface inspection system structured in accord with the principles of the instant invention.

Referring now to FIG. 1, there is shown a block diagram illustrating various components of a coated surface characterizing system of the instant invention. The system includes a sensor head, the components thereof which are located within the broken line 10 as well as signal processing means disposed outside that line. The sensor head is adapted to measure a plurality of characteristics of the coated surface and provide a signal corresponding to the value of each of said characteristics. As illustrated herein, the head includes four sensor units 12, 14, 16 and 18 adapted to measure the parameters of color, gloss, film build and distinctness of image respectively. There are a wide variety of such sensors available to measure the foregoing parameters and one of skill in the art may, without undue experimentation select and adapt such sensors for use in the present invention.

Color is measured by the first sensor unit 12. There are a number of apparatus adapted to measure color and a number of scales upon which such measurements may be quantified, the precise choice of such apparatus and measurement scale will be dependent upon particular material application. The present invention may advantageously function utilizing either the L*a*b* scale, the CIE 1976 scale or the Y x y scale with differences. The L*a*b* scale quantifies color by a set of "a" coordinates denominating the red/green value of the color, a set of "b" coordinates denominating the blue/yellow value and an "L" value indicative of the lightness or darkness of the color. Utilizing such a scheme colors may be quantified in a three-dimensional parameter space. Obviously other such quantifications may be employed. Measurement of the color values is readily accomplished by color sensitive photosensors as for example in colorimeters, spectrophotometers and the like. One color sensor having particular utility is the model CR131, manufactured by the Minolta Corporation.

Gloss is a measurement of specular reflection from a surface and is responsible for a mirror-like appearance. Gloss is readily quantified by an instrument called a gloss meter which measures gloss as a function of the amount specular versus diffuse reflection of a material. Gloss measurements are often specified by the angle at which the measurement is made. Typical gloss measurements are made at twenty and thirty degrees and are referred to as "gloss-20" and "gloss-30."

Distinctness of image is a measure of the sharpness with which patterned images are reflected by the surface of an object and in this regard is related to gloss. Some particular techniques for the measurement of gloss and distinctness of image are disclosed in U.S. patent application Ser. No. 899,467 filed Aug. 22, 1986 now issued as U.S. Pat. No. 4,761,676 and entitled "Fault Detection and Reset in Surface Reflectance Meter", the disclosure of which is incorporated herein by reference.

Film build is a measurement of the thickness of the coating. There are a wide variety of sensors available for such measurements. Thickness sensors rely on a variety of optical and electrical phenomena such as interference, capacitance magnetic fields or the like and can be readily adapted by one of skill in the art to interface with the present invention. It is generally required that a film thickness sensor 16 be capable of reading thicknesses on ferrous substrates and be capable of providing thickness measurements for the range of 0.000 to 0.015 inches.

Proper placement of the sensor head upon the coated surface being characterized is important if accurate readings are to be obtained. Therefore the head will preferably include a position indicator to indicate proper placement thereof. The position indicator will have one or more transducers, such as mechanical, optical or electronic transducers associated therewith. In one embodiment, each individual sensor 12, 14 16 and 18 has associated therewith a transducer to indicate its proper placement, and such transducers activate a visual display 31, such as a L.E.D. display on the face of the head.

The sensor units 12, 14, 16 and 18 communicate with a microprocessor 20. The microprocessor 20 also has associated therewith a plurality of control switches such as a select switch 22, a transmit switch 24, a trigger switch 26, a configuration switch 28 and a display device 30, the function of which will all be elaborated on hereinbelow.

The microprocessor 20 in the sensor head communicates with a signal processing computer 32 via a serial data line 34, which is typically a 4800 baud line, it being understood that infrared data links, radio links and the like may be likewise employed. As depicted an expander 36 is also disposed in the link between the microprocessor 20 and the signal processing computer 32. Use of such an expander 36 is particularly advantageous when a plurality of sensor heads are employed in the characterizing and monitoring system of the instant invention. In such instances, the expander serves to mediate communication between the separate microprocessors of each head and the signal processing computer 32, as will be discussed in greater detail hereinbelow.

The signal processing computer 32 may have a number of peripheral devices associated therewith. As depicted in FIG. 1, the signal processing computer 32 has a display 38, an input device 40, a printer 42, an alarm device 44 and a memory storage device 46 associated therewith, it being kept in mind that a plurality of such peripheral devices, or peripheral devices other than those disclosed may likewise be employed in keeping with the present invention.

The exact operational sequence of the system of the present invention will depend upon particular applications. For example, the system may be utilized in a production mode to inspect coated parts as for example, body panels of automobiles; likewise, the system may be employed to gather and display data as for example in an R & D situation.

Configuration of the system for particular applications is readily accomplished by the signal processing computer 32 upon initialization. For example, a light pen, keyboard, or other such input device 40 may be employed in conjunction with the display 38 to set the operational parameters of the system. These parameters may include for example, particular measurements to be made by the sensor heads 12, 14, 16 and 18 as well as the sequence in which they are to be made. Initialization may also select a data base with which to compare the measured parameters as well as establishing limits for the amount of deviation from said parameters. Initialization may also select a sequence of measurements to be applied to a particular item. As for example, an automobile may have a plurality of sets of readings taken by the head in a given order such as readings from the hood, fenders, doors and trunk lid. Values taken from the various portions of the automobile may then be compared to assess color match or other such quantifiable values.

The signal processing computer 32 has associated therewith a memory storage unit 46, which may comprise, for example, a 10 megabyte hard disk as well as one or more auxiliary floppy disks. The memory storage unit 46 provides nonvolatile storage for the various data bases utilized to effect comparisons as well as the subroutines used for initializing the system. Additionally, the memory storage unit 46 may accumulate data generated during operation of the system so as to provide new data bases with which to effect comparisons.

Once initialization is complete and the appropriate data bases and operational sequences and routines have been selected, the system is ready for operation. An operational sequence is begun by placing the sensor head against the surface to be measured and depressing the trigger button 26, which is preferably conveniently located as for example on the gripper handle of the sensor head. In those instances where the sensor head includes a position indicator, this unit will alert the operator to proper placement of the head, by an audio prompt on a visual display, as for example a L.E.D. display on the control panel of the head. The trigger button 26 signals the microprocessor to begin the reading sequence and the microprocessor in turn activates one or more of the sensor units 12, 14, 16 and 18. It should be noted at this point that in some instances all the sensors will be employed to take a reading whereas in other instances a particular measuring routine may employ fewer sensors. As mentioned previously, the sensors are selected during initialization; alternatively, selection of the sensors may be accomplished by manual selection at the sensor head. Upon activation by the microprocessor 20 the selected sensors read their respective parameters and generate a signal which is communicated back to the microprocessor 20. The microprocessor 20 in turn recognizes each of the signals and formats them for transmission to the signal processing computer 32. Formatting may involve conversion of the signal to analog to digital form. For example, the film thickness monitor 16 typically generates analog signals and accordingly the microprocessor 20 digitizes such a signal prior to transmission. The microprocessor 20 includes a buffer therein for temporary storage of the formatted signal prior to transmission. Activation of the transmit switch 24 signals the microprocessor 20 to transmit the signal via the serial line 34 to the signal processing computer 32. In those instances where an expander 36 is included, the signal from the microprocessor 20 is received by the expander.

As is best shown in FIG. 3, the expander 36, which may be a Versatile Expander, Model 1867 manufactured by ATI Systems, Inc., Madison Heights, Mich. is most advantageously employed in those instances where a plurality of sensor heads 10a, 10b, 10c, 10d are utilized in conjunction with a single processing unit 37. The expander 36 may be configured to perform a number of valuable functions. For example, the expander 36 may include buffer memory 48 for storing signals generated by microprocessor 20, until they are called for by a signal processing computer 32 at which time the expander 36 identifies a signal as to which head it originated from and transmits that signal to the signal processing computer 32. While the expander may be configured so as to recognize and identify signals from a number of heads it is generally more advantageous to make the expander a "transparent" device and instead include a configuration switch 28 in each of the heads, which switch may be set to designate that particular head as being number 1, 2, 3 and so forth; in such instances then, the head will identify the signal provided thereby. The expander may also be modified to operate as a power supply adapted to supply electrical power to the sensor head via the serial line 34.

The signal processing computer 32 receives a signal from the microprocessor 20 either directly or via the expander 36 and upon receipt of that signal processes it in accord with the preselected operational routine. As mentioned previously, processing can involve comparison with data bases generated either by previous readings or from input parameters, as for example manufacturer's product specifications for paint finishes. Comparison with the data base enables an assessment of the acceptability of the coated surface. The signal processing computer 32 makes this comparison, stores the results and provides an indication if the coated surface is not acceptable. Such indication may be provided by printing a message on the printer 42, displaying a message on the display 38 or sounding the alarm 44. Additionally, the signal processing computer 32 may further process the results, as for example by generating statistical data in the form of graphs, tables and the like. The signal processing computer may also communicate with another computer at a remote location for purposes of inventory control, statistical analysis and the like.

The signal processing computer 32 may be programmed during initialization to respond to the signal received from the sensor head by selecting an appropriate data base for comparison of the measured parameters therewith. For example, the signal processing computer 32 may read a color signal from the sensor head microprocessor 20 and recognize that the sensor head is measuring the parameters of a red painted object. The signal processing computer 32 then selects the appropriate data base from memory storage 36 and utilizes that data base to asses the acceptability of other parameters, such as gloss, distinctness of image and film thickness.

Operational sequences other than the one described may similarly be implemented. For example, the select switch 22 associated with the microprocessor 20 in the sensor head may be employed to select which of these sensor units 12, 14, 16 and 18 are being read at a particular time. Likewise, the display 30 associated with the microprocessor 20 may be utilized in conjunction with the selector switch to measure and display particular parameters without the necessity of transmitting those parameters back to the signal processing computer 32. Such a manual mode of operation may be useful in an R and D situation where data is gathered and assessed directly at the point where the sensor head is employed.

Other such modifications will be readily apparent. For example, the signal processing computer 32 may be programmed to recognize and respond to a particular code number designating either a particular model of automobile or a particular type of paint on an automobile. This identification number may be input either by use of the input device 40, associated with the computer 32 or by a similar type of input device associated with the sensor head. This code number, when received by the signal processing computer 32 will call up a data base for comparison of measured parameters therewith or alternatively may call up an entire subroutine of measurements, such as the sequence of body parts to be measured. Such a sequence may be communicated with the system operator via the display 30 on the sensor head or the display 38 associated with the signal processing computer 32. In yet other modifications of the system, there may be included a greater or lesser number of sensor units 12, 14, 16 and 18 either adapted to measure yet other parameters, or functioning as duplicates of certain sensors so as to enable plural readings of particular parameters to be made. For example, the system may include several gloss meters as for example one gloss meter adapted to measure the gloss at a 20° angle and another adapted to measure gloss at a 30° angle so as to better assess the amount of specular versus diffuse reflection.

Figure 2:
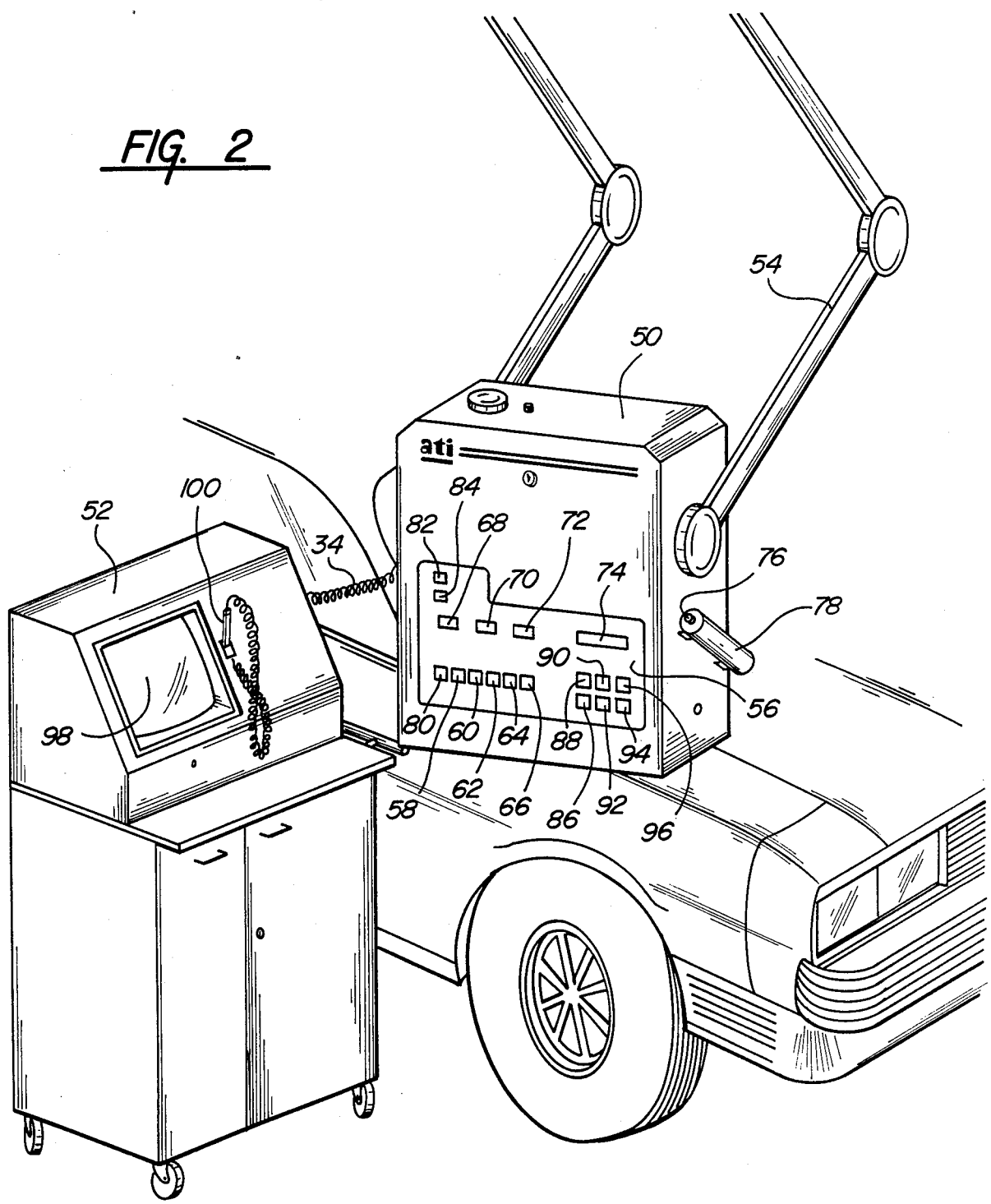
FIG. 2 is a perspective view of the physical embodiment of one particular system of the instant invention as disposed to characterize and monitor the painted surface of an automobile.

As mentioned previously, the system disclosed herein may be adapted to characterize and monitor a variety of coated surfaces. However, one important use is in the mass production of automobiles. FIG. 2 illustrates one specific embodiment of the invention as adapted for the production of automobiles. FIG. 2 illustrates a coated surface film characterization system which includes a sensor head 50 and a processing console 52 interconnected by a cable 34. These items generally include the components discussed with reference to FIG. 1.

It will be noted that the sensor head 50 is mounted on a support bracket 54 to enable ready positioning thereof. It is preferred that this support bracket 54 be a counterbalanced bracket provided with springs, weights or other such means for allowing ready and easy positioning.

Referring specifically to the sensor head 50 it will be noted that there is included a control panel 56 having a plurality of control switches and display elements thereupon. A first set of control switches activate the various functions of the sensor head and generally correspond to the select means 22 described with reference to FIG. 1. Included in this group of switches are the gloss 20, 58, gloss 30, 60, D.O.I. 62, film build 64 and color 66 switches. In those situations where the operational sequence of the machine is to be configured from the sensor head itself, these switches are pressed in order to select which sensors will operate during the read cycle of the head. Each of these functions has associated therewith a display element 68, 70, 72 and 74. It will be noted that the gloss display element 68 functions to display gloss for both the gloss 20 and gloss 30 measurements. The sensor head 50 further includes a trigger button 76 mounted on the handles 78 thereof. As discussed with reference to FIG. 1, the trigger activates the sensors so as to take the preselected readings.

The sensor head 50 further includes a transmit button 80 which is used to send selected data on to the computer in the console 52. The sensor head 50 of this particular embodiment further includes a ready indicator 82 for purposes of indicating that the sensor head 50 is in a standby mode and an in progress indicator 84, indicative of the fact that data is being read or is being held for transmission.

An additional set of control switches are located on the right side of the control panel 56 and are employed in this embodiment to activate and calibrate the color sensor unit which may for example be a Minolta CR131. Switch number 86 activates the color sensor, while switches 88 and 90 are utilized for calibration. The remaining switches 92, 94, and 96 are employed to configure the color sensor. Once activated and configured the color sensor may be selected as previously mentioned by the use of the selector button 66.

The remainder of the system is enclosed within the console 52. Included in the console is a display screen 98 having a light pen 100 associated therewith. The screen 98 and the pen 100 are utilized to input data to the system for selection of data bases, operational programs and routines and the like.

As mentioned previously, the keyboard may be used either in conjunction with, or instead of the light pen 100 for data input. The base of the console 52 includes a cabinet adapted to house the computer, disk drive and printer. If an expander is utilized in this system, it may either be located in the base of the console 52 or may be disposed at a location central to the plural sensor heads employed so as to eliminate excess cable connections to the console 52.

It should be readily apparent that while the present invention has been described with reference to a system for characterizing a painted surface, the principles thereof are equally applicable to the measurement and characterizations of other surfaces such as plated, or anodized surfaces, or to the surfaces of plastics and the like. Obviously, among other configurations of the system of the present invention are possible depending upon particular applications being addressed. In light of the foregoing such modifications should be readily apparent to one of skill in the art. It will thus be appreciated that the discussion, drawings and descriptions are merely meant to be illustrative of the general principles of the instant invention. It is the following claims, including all equivalents, which are meant to define the scope of the invention.

We claim:

1. A system for characterizing and monitoring a coated surface, said system including:

a sensor head including a plurality of sensor units, each operative to sense at least one characteristic of the coated surface and provide a signal corresponding to the value of each of said characteristics, said sensor head operative to convey said signal from said plurality of sensor units to signal processing means; and, said signal processing means operative to:
(a) receive the signals provided by said sensor head,
(b) analyze the signals to determine the values of the sensed characteristics of the coated surface;
(c) compare the determined values of the sensed characteristics with stored data corresponding to characteristics of an acceptable surface so as to assess the acceptability of the coated surface;
(d) store the results of said comparison; and,
(e) provided an indication if the coated surface is not acceptable; and, wherein said sensor head includes four sensor units therein operative to measure gloss, distinctness of image, film build and color respectively, whereby said system is operative to characterize and monitor a painted surface.

2. A system as in claim 1, wherein said sensor head further includes a configuration switch operable to select which of each of said four sensors will be activated.

3. A system as in claim 1, wherein said sensor head includes a microprocessor having a buffer memory operative to store the signals from the sensor units for later transmission to said signal processing means.

4. A system as in claim 1, wherein said sensor head further includes a microprocessor operative to receive the signals from the sensor units and format said signals.

5. A system as in claim 1, wherein said sensor head further includes a display device operative to display at least one the values of the sensed characteristics of the coated surface.

6. A system as in claim 1, wherein said signal processing means further includes a computer.

7. A system as in claim 6, wherein said signal processing means further includes a multiplex expander in communication with said computer.

8. A system as in claim 7, further including a plurality of sensor heads; and wherein said expander is operative to receive the signals provided by each of said heads, store said signals and transmit said signals to the computer.

9. A system as in claim 7, wherein said expander is further operative to provide electrical power to said sensor head.

10. A system as in claim 1, wherein said signal processing means comprises a computer having memory storage associated therewith for storing a plurality of data bases therein.

11. A system as in claim 10 wherein said signal processing computer includes a program operative to select one of said stored data bases in response to said signals conveyed thereto from said sensor head.

12. A system as in claim 10, wherein said signal processing computer includes a program operative to select one of said data bases in response to user input.

13. A system as in claim 1, wherein said signal processing means comprises a computer programmed to convey to, and store in another computer, signals generated by the sensor head.

14. A system as in claim 1, wherein said signal processing means is operative to provide an audible indication if the coated surface is not acceptable.

15. A system as in claim 1, wherein said sensor head has associated therewith position indicator means operative to indicate the proper placement of said head upon the coated surface.

16. A system for characterizing and monitoring a painted surface, said system including:
a sensor head including four sensor units therein for measuring the characteristics of gloss, distinctness of image, film build and color respectively, and each operative to provide a signal corresponding to a particular one of said characteristics, said sensor head further including a display device operative to display the values of said characteristics, buffer means for storing the signals corresponding to said characteristics and transmit means operative to send said signals to downstream signal processing means;
signal processing means including a computer, display device, input device and data storage means, said signal processing means operative to:
(a) receive the signal provided by the sensor head;
(b) analyze the signal to determine the values of gloss, distinctness of image, film build and color;
(c) compare at least one of said determined values with data from said storage means so as to assess the acceptability of the painted surface;
(d) store the result of the comparison in said storage means; and
(e) provide an indication if the coated surface is not acceptable.

17. A system as in claim 15, wherein said gloss sensor unit is operative to measure 20 degree gloss and 30 degree gloss.

* * * * *